(12) United States Patent
Deger et al.

(10) Patent No.: US 6,274,325 B1
(45) Date of Patent: *Aug. 14, 2001

(54) METHOD FOR CARRYING OUT A HOMOGENEOUS-IMMUNOASSAY BASED ON AGGLUTINATION

(75) Inventors: Arno Deger, Seeshaupt (DE); François Guillot, Meylan (FR); Michael Berger, Penzberg; Dittmar Schlieper, Weilheim, both of (DE)

(73) Assignee: Boehringer Mannheim GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/314,432

(22) Filed: Sep. 28, 1994

Related U.S. Application Data

(63) Continuation-in-part of application No. 08/071,593, filed on Jun. 3, 1993, now abandoned, which is a continuation of application No. 07/718,798, filed on Jun. 21, 1991, now abandoned, which is a continuation-in-part of application No. 08/715,593, filed on Jun. 21, 1991, now abandoned.

(30) Foreign Application Priority Data

Jun. 25, 1990 (DE) .................................. 40 20 204

(51) Int. Cl.[7] ........................ G01N 33/53; G01N 33/566; A61K 39/395
(52) U.S. Cl. ................................ 435/7.1; 435/7.5; 435/4; 436/501; 436/518; 436/526; 424/178.1; 424/179.1
(58) Field of Search ................... 435/7.1, 7.5, 4; 436/501, 512, 524, 527, 533, 518, 526; 424/178.1, 179.1

(56) References Cited

U.S. PATENT DOCUMENTS

| | | | |
|---|---|---|---|
| 4,232,119 | * 11/1980 | Carlsson | 435/7.1 |
| 4,582,810 | * 4/1986 | Rsenstein | 436/528 |
| 4,867,973 | * 9/1989 | Goers et al. | 424/85.91 |
| 4,914,040 | 4/1990 | Lenz et al. | 435/175 |
| 4,942,136 | * 7/1990 | Konishi | 436/512 |
| 4,983,529 | * 1/1991 | Stewart et al. | 436/512 |
| 5,002,885 | * 3/1991 | Stavrianopoulos | 435/188 |
| 5,221,605 | * 6/1993 | Bard et al. | 435/4 |
| 5,378,608 | * 1/1995 | Marui et al. | 435/7.5 |

FOREIGN PATENT DOCUMENTS

| | | |
|---|---|---|
| 0307754 | 3/1989 | (EP) . |
| 0331068 | 9/1989 | (EP) . |
| 0349988 | 1/1990 | (EP) . |
| 0356964 | 3/1990 | (EP) . |
| WO 90/05301 | 5/1990 | (WO) . |

* cited by examiner

*Primary Examiner*—Padmashri Ponnaluri
(74) *Attorney, Agent, or Firm*—Fulbright & Jaworski, LLP

(57) ABSTRACT

The invention concerns a homogeneous immunoassay based on agglutination using an Fab'-biotin material and agglutinatable particles which carry streptavidin or avidin. The invention also concerns the Fab'-biotin which is bound or linked via linkage groups to a label compound which can electrochemiluminescence and the particles having avidin or streptavidin on their surface are magnetic.

14 Claims, No Drawings

METHOD FOR CARRYING OUT A HOMOGENEOUS-IMMUNOASSAY BASED ON AGGLUTINATION

RELATED APPLICATION

This application is a continuation-in-part of Ser. No. 08/715,593, filed Jun. 21, 1991, now abandoned Jan. 26, 2000.

This application is a continuation-in-part of application Ser. No. 08/071,593, filed Jun. 3, 1993, now abandoned which is a continuation application of Ser. No. 07/718,798, filed Jun. 21, 1991, now abandoned.

DESCRIPTION

The invention concerns a method for carrying out a homogeneous immunoassay based on agglutination in which a conjugate of an Fab' fragment and a component K is used.

Very many substances occur in body fluids and tissues which are capable of binding to a specific binding partner and which serve as parameters for certain diseases or the state of health of the human body. These include on the one hand immunologically active proteins which have binding sites on their surface such as e.g. tumour markers, hormones or viral proteins and on the other hand, DNA fragments. Since these substances often only occur in very small amounts, methods based on immunoassays are used for their detection with which these substances can be determined very specifically and exactly. There are many variants of these methods. The various immunological methods of determination may be classified into homogeneous and heterogeneous methods. A solid phase reaction always forms part of the heterogeneous method in order to immobilize complexes which contain the substance to be detected and a labelled component and thus to separate them from unbound components. In the homogeneous method variant there is no separation of bound label and unbound label so that bound and unbound label have to be differentiated by other methods.

There are different methods for this.

A method for the detection of proteins is known from DE-OS 27 49 956 which is based on the evaluation of an agglutination reaction. In this method antibodies against the substance to be detected are bound directly to the agglutinatable particles. However, the reactivity of the antibodies can be impaired by this binding. In addition such a method of determination is susceptible to interference by rheumatoid factors.

A homogeneous method of detection is described in US patent application Ser. No. 07/396,860 (22.08.89), now U.S. Pat. No. 5,362,655, which already overcomes the disadvantages of the previously known methods. In this method the sample solution is incubated with at least two receptors which are capable of binding to one another and of which one can bind to the substance to be detected. In this method an agglutination can only take place when the substance to be detected binds to both receptors and not, however, when the receptors bind to one another or the substance to be detected binds to only one of the two receptors. Conjugates consisting of one partner of a pair which specifically bind to one another and a component K capable of specific binding to the substance to be detected are used as the receptors capable of binding to the substance to be detected. If the method described here is used for the detection of proteins which have several identical epitopes then a conjugate has to be used as the receptor capable of binding to the substance to be detected which only has a single binding site for the substance to be detected in order to prevent an unspecific agglutination.

The prior art also mentions electrochemiluminescence labels useful in detection of an analyte. In that regard EP 580 979 based on U.S. application Ser. No. 666,987, now abandoned and Ser. No. 789,113 now U.S. Pat. No. 5,238, 808 filed Oct. 31, 1984 and Oct. 24, 1985 respectively (also known as EP 199804), WO 87/06706 based on U.S. application Ser. No. 858,354, now abandoned, filed Apr. 30, 1986, WO 92/14138 based on U.S. application Ser. Nos. 652,427, now abandoned and 827,269, now U.S. Pat. No. 4,953,073, filed Feb. 6, 1991 and Feb. 3, 1992 respectively, WO 90/05301 based on U.S. application Ser. No. 266,882, now abandoned, filed Nov. 3, 1988 and WO 90/11511 based on U.S. application Ser. No. 325,459, now U.S. Pat. No. 5,068,88 filed Mar. 17, 1989 provide general information about these assays and are hereby incorporated by reference.

The object of the present invention was to provide a method for carrying out homogeneous immunoassays in which unspecific agglutinations are avoided as far as possible in order that exact and reproducible results are obtained.

This object is achieved by a method for carrying out a homogeneous immunoassay based on agglutination in which a conjugate of a Fab' fragment and a component K is used, which is characterized in that a conjugate is used which is obtained by subjecting a F(ab')$_2$ fragment of an antibody of the immunoglobulin G class to reducing conditions and subsequently reacting it with the component K which either has a functional group suitable for the binding or was derivatized in a suitable manner by introduction of a functional group whereby the component K is bound via the functional group to the free SH group of the Fab' fragment formed during the reduction and agglutinatable particles are used which carry a substance capable of binding to K.

Surprisingly it was found that unspecific agglutinations can be avoided to a large extent by using these conjugates. Methods based on agglutination immunoassays could be further improved with regard to accuracy and reproducibility by using the monovalent binding partners.

Conjugates consisting of a Fab' fragment of an IgG antibody which is capable of specifically binding to the substance to be detected and a component K are used for the method according to the present invention. Such conjugates can be produced by treating the antibody which is to be used in each case with pepsin in a known way. In this process fragments denoted F(ab')$_2$ are formed which have two paratopes and in which the two heavy chains are held together by disulfide bridges. The F(ab')$_2$ fragments are then subjected to mild reducing conditions so that the intramolecular disulfides are preferentially cleaved in the hinge region but not, however, the disulfide bridges between the light and heavy chain. Therefore, the reduction is preferably carried out with a mild reagent. Cysteamine, cysteine, mercaptoethanol or boron hydride are e.g. suitable for this. In this way Fab' fragments are obtained which have 1 to 3 free SH groups. All free SH groups are available for binding to the components used. It has, however, turned out that, because of steric hindrance, either one component is bound or only one of two or more bound components retains its activity.

A component K which is a partner of a specific binding pair is bound to these Fab' fragments. The component K can be bound to the Fab' fragment either via a functional group which is already present or which is introduced or which is activated, if desired. The binding either takes place directly between SH groups of the Fab' fragment and a functional group of the component K or via a spacer.

The binding of the Fab' fragment and component K can take place directly via the functional groups present in each case. In this form of the method the proportion of unspecific linkages is particularly small. It is also possible to use a spacer for the binding. The length of the spacer depends in this case on the position of the free SH groups which is in turn dependent on the subclass of the IgG antibody used. It was found that up to three component molecules can be bound but that because of steric hindrance only one of them is capable of binding to the partner of the specific binding pair.

Bifunctional compounds which have a functional group which is capable of binding to the SH group and a second functional group which can be the same or different and which can covalently bind to the component are suitable as the spacer. The length of the spacer depends on the position of the SH bonds and thus on the subclass of the antibody from which the fragment is derived. If the spacer is too long it has the effect that even when several SH groups are relatively close together, a binding to all components is possible since the steric hindrance is overcome. The length of the spacer is therefore dependent on the position of the SH bonds and is thus defined by the Fab' fragment used and is in the range of 4 to 16 atoms preferably 4 to 8 atoms for Fab' fragments of the IgG subclass I, and in the range 4 to 10 atoms, preferably 4 to 6 atoms for Fab' fragments of antibodies of the subclass IgG II. Maleimidobutyllysine is preferably used for the production of conjugates consisting of a component K and a Fab' fragment of an IgG antibody of the subclass I and maleimidoethylamine is preferably used for conjugates containing Fab' fragments of the IgG subclass II.

The conjugate of Fab' fragment and component K is used in a known manner as the receptor when carrying out a homogeneous immunoassay. In the method according to the present invention agglutinatable particles which carry a substance capable of binding to the component K are used as an additional receptor. In a preferred embodiment agglutinatable particles are used to which a substance capable of binding to the component K is covalently bound by means of a bifunctional photoreactive spacer. Such agglutinatable particles can be produced by first reacting the substance capable of binding to the component K with a heterobifunctional reagent which has an arylazide group on one side and a functional group which is reactive with amino groups of the binding partner on the other side. In this process this group which is reactive with amino groups reacts with the bindable substance. After removing non-reacted reagent, the biological material is brought into contact with the inert carrier material which can for example be a polystyrene latex with a particle size below 100 nm, for a pre-determined period and then the photoreaction is triggered by the action of light whereby the binding to the inert carrier takes place via formation of a reactive nitrene from the arylazide group. Subsequently non-covalently bound material is effectively detached by washing with detergent and removed by centrifugation procedures or dialysis on membranes. The surface properties of such particles can be specifically modified by e.g. applying an immunologically inert protein such as e.g. BSA onto these particles by pre-, co- or recoating. The stability of the reagent is also increased by this means. The proportion of specifically bindable substance per particle is defined by the amount of protein as well as the latex concentration used for the coating and can be adjusted reproducibly. In addition a surface with a defined specific bindability can be regulated by selection of the heterobifunctional reagent or its chain length. An advantage of this process is that the specifically bindable substance can be bound to any type of solid phase i.e. it does not rely on solid phase particles with functional groups. Homopolymers and copolymers of styrene and methylstyrene, of acrylic acid and its esters, of methacrylic acid and its derivatives such as acrylonitrile or acrylamide and of dienes such as butadiene, chloroprene or isoprene and vinyl chloride are particularly suitable as the solid phase. Undesired latex-latex linkages virtually do not arise because of the type of linkage but rather only the covalent linkage of latex and protein occurs as a result of the unspecific reaction of the azido group and to a slight extent a linkage of protein with protein. The substance bound to the agglutinatable particles and the component K are capable of binding to one another. All pairs which specifically bind to one another are suitable for this. Streptavidin or avidin and biotin are preferably used as component K and thus as the bindable substance.

When the method is carried out, i.e. when the sample solution is incubated with the conjugate and with the agglutinable particles, on the one hand the substance to be detected binds to the Fab' fragment of the conjugate and on the other hand the component K of the conjugate binds to the agglutinable particles. An agglutination can only be triggered by these linkages. Since the conjugate is monovalent with respect to binding to the substance to be detected and with respect to binding to the agglutinable particles, an agglutination cannot take place via the receptors per se. The more substance to be detected present in the sample solution, the greater is the agglutination. The amount of agglutination, which can be detected according to known methods, is therefore a direct measure of the content of substance to be detected.

The method according to the present invention is particularly suitable for embodiments as described in US patent application Ser. No. 375,746 now U.S. Pat. No. 5,071,767 issued Dec. 10, 1991 and hereby incorporated by reference or in U.S. Pat. No. application Ser. No. 396,860 (22.8.89) hereby incorporated by references. They describe homogeneous immunoassays in which a sample solution containing the substance to be detected is incubated with at least two receptors, one of which is a conjugate of a partner of a specific binding pair and a component which binds specifically to the substance to be determined and the other receptor has at least two binding sites for the specific binding partner. Incubation of the sample solution with the two receptors results in binding of the conjugate to the substance to be detected and to the other receptor which causes an agglutination. Only those complexes in which the substance to be detected and both receptors are bound can agglutinate. In order to increase the accuracy, it is preferable to use a conjugate with monovalent components with respect to the binding.

A further object of the invention is to use Fab'-biotin fragments according to the invention in immunoelectroluminescent assays. General information as to the above electrochemiluminescence processes in general is found in the EP 199 804, EP 580 979, WO 87/06706, WO 90/05301, Wo 90/11511 and WO 92/14138 applications as referred to above.

Here the Fab' fragment is linked to biotin to form a monobiotinylated Fab' fragment and a binding partner of the analyte or the analyte or an analog of the analyte are linked to a label compound capable of being induced to electrochemiluminescence.

It will be understood that the specification and examples are illustrate but not limitative of the present invention and that other embodiments within the spirit and scope of the invention will suggest themselves to those skilled in the art.

The invention is elucidated by the following examples:

EXAMPLE 1
Preparation of streptavidin-latex

Streptavidin (Boehringer Mannheim) was dissolved at a concentration of 10 mg/ml in 50 mM $K_2HPO_4$, pH 8.0. Subsequently a solution of N-hydroxysuccinimidyl-4-azidobenzoate (HSAB) in DMSO was added in the dark such that a molar ratio of 10:1 (HSAB:streptavidin) results. It was incubated at 25° C. for two hours in the dark. Subsequently excess HSAB was removed by dialysis in the dark.

In order to coat the lattices with streptavidin, a 1% suspension of polystyrene particles (Dow<100 nm) was incubated overnight in the dark with the activated streptavidin (1 mg/ml, production see above). Subsequently the particles were irradiated with UV light (340 nm). The streptavidin lattices were washed twice with 50 mM glycine, pH 7.5 and then incubated for 16 hours with a recoating solution (0.1% BSA). After a further washing step with 50 mM glycine, pH 7.5 the streptavidin latices were stored in glycine buffer at 4° C.

EXAMPLE 2
Production of Fab'-biotin conjugates

Monoclonal antibodies of the immunoglobulin class G I and G IIa, which were obtained in the usual way by immunization of mice, were converted into Fab'-biotin conjugates according to the method described in the following:

50 mg mouse IgG was dissolved in 100 mM sodium citrate, pH 3.6 to a protein concentration of 10 mg/ml. A pepsin solution (1 mg/ml in 100 mM sodium citrate, pH 3.6) was added in a ratio 1:1000 to the solution which was heated to 37° C. After stirring for 2.5 hours at 37° C. the pH of the reaction mixture was adjusted to 8.3 by addition of Tris. Subsequently it was dialyzed against 20 mM Tris/HCl, pH 7.8. The separation of undigested IgG and Fc fragments from F(ab')$_2$ was carried out by chromatography on DEAE Sepharose fast flow and Sephacryl S-200. The F(ab')$_2$ fragments were collected and lyophilized.

10 mg F(ab')2 was dissolved in 100 mM $KH_2PO_4$, 1 mM EDTA, pH 6.3 at a concentration of 10 mg/ml. Subsequently 20 Al of a solution of 500 mM sodium arsenite, 1 mM EDTA, 100 mM $KH_2PO_4$, pH 6.8 as well as 25 $\mu$l of a solution of 200 mM mercaptoethylamine, 1 mM EDTA, 100 mM $KH_2PO_4$, pH 6.8 were added. It was incubated at 37° C. for 2 hours while stirring. Subsequently the Fab' pool was separated from lower molecular components by chromatography on a Sephadex G-25 column. Maleimidoethylamine biotin and maleimidobutyryllysine-biotin were each dissolved at a concentration of 1 mg/ml in DMSO for the biotinylation. In separate preparations maleimidoethylamine biotin or maleimidobutyryllysine-biotin were added to a solution of the Fab' fragments in such a way that a molar ratio of 10:1 (biotin derivative: Fab') resulted. After incubating for one hour at 25° C. cysteine was first added to a final concentration of 1 mM and after a further 30 minutes iodoacetamide was added to a final concentration of 5 mM. After a further incubation of 30 minutes it was dialyzed against 2 mM $KH_2PO_4$, pH 7.5. The Fab'-biotin conjugates obtained were stored at −20° C.

EXAMPLE 3

It was investigated to what extent the unspecific agglutination is reduced by using the conjugates according to the present invention in a test using latex particles coated with streptavidin and conjugates of anti-TSH antibody fragments and biotin.

A monoclonal anti-TSH antibody of the immunoglobulin class G I (ECACC 87122202) was used. For comparison a complete antibody was biotinylated via the amino groups of the antibody according to JACS 100 (1978), 3585–3590 hereby incorporated by references by reaction with N-hydroxysuccinimide-X-biotin in a ratio of 7:1 (biotin:IgG).

The Fab'-biotin conjugate according to the present invention was produced from this antibody using maleimidobutyryllysine-biotin as described in Example 2.

In order to determine the agglutination, 60 $\mu$l 1% streptavidin-latex (production see Example 1), 800 $\mu$l loo mM Tris/HCl, pH 8.0 and 20 $\mu$l anti-TSH-IgG-biotin conjugate (comparison) or 20 $\mu$l anti-TSH-Fab'-biotin conjugate (according to the present invention) were pipetted into cuvettes of a Perkin-Elmer photometer. The protein concentration of the conjugates was in each case 10 $\mu$g/ml.

The increase in absorbance at 405 nm was measured between t=1 min and t=10 min.

The result is shown in Table 1. It showed that the unspecific agglutination could be reduced to less than ⅕ by using the Fab'-biotin conjugate according to the present invention of the reference value (IgG-biotin conjugate).

TABLE 1

| Antibody conjugate | Increase in absorbance (mA) |
| --- | --- |
| IgG-biotin (comparison) | 663 |
| Fab'-biotin (according to the present invention) | 119 |

EXAMPLE 4

The unspecific agglutination of conjugates produced according to the present invention was examined as described in Example 3.

Two different monoclonal anti-myoglobin antibodies, which both belong to the immunoglobulin class IgG I, were converted into Fab'-biotin conjugates as described in Example 2. In order to investigate the influence of the spacer length on the unspecific agglutination, both Fab' fragments were reacted with biotin using maleimidoethylamine (MEA) and maleimidobutyryllysine (MBL) as spacer.

The results are summarized in Table 2. It is clear that the unspecific agglutination can be reduced even further by using the shorter MEA spacer.

TABLE 2

| Antibody conjugate | Increase in absorbance (mA) | |
| --- | --- | --- |
| (Fab'-biotin) | MBL | MEA |
| Anti-myoglobin-Ab 1 | 267 | 88 |
| Anti-myoglobin-Ab 2 | 228 | 72 |

EXAMPLE 5

Two different monoclonal anti-AFP antibodies, one of which belongs to the immunoglobulin class G I (Mab LJ738) and the other to the class G IIa (Mab Tull, ECACC 87041002), were converted into Fab'-biotin conjugates as described in Example 2. In this process both Fab' fragments were biotinylated with biotin using MEA or MBL as spacer.

In order to determine the unspecific agglutination, 20 µl of each of the different conjugates (10 µg/ml), 800 µl 100 mM Tris/HCl, 2% PEG 40000, 2% Pluronic F68, pH 7.0 and 20 µl 1% streptavidin-latex (production see Example 1) were pipetted into the cuvettes of a Perkin-Elmer photometer. The increase in absorbance was measured at 405 nm between t=1 min and t=10 min.

The results are shown in Table 3. As already measured for the other monoclonal antibodies of the immunoglobulin class I (cf. Examples 3 and 4), a low unspecific agglutination was also obtained with the anti-AFP-Fab'-biotin from IgG I which could be suppressed even further by using the shorter MEA spacer.

In contrast the anti-AFP-Fab'-biotin conjugate from the IgG IIa resulted in a relatively high unspecific agglutination with the MBL spacer. However, more favourable results could be obtained by using the shorter MEA spacer.

TABLE 3

| Antibody conjugate | Increase in absorbance (mA) | |
| --- | --- | --- |
| (Fab'-biotin) | MBL | MEA |
| Anti-AFP-Mab-LJ738 (IgG I) | 42 | 3 |
| Anti-AFP-Mab-Tull (IgG IIa) | 434 | 212 |

EXAMPLE 6

A homogeneous immunoassay based on streptavidin-latex was carried out with the conjugates Mab-Tull-Fab'-MEA-biotin and Mab-LJ738-Fab'-MBL-biotin: 50 µl of a solution of both conjugates (10 µg/ml, ratio of the antibody conjugates of 1:1), 800 µl 100 mM Tris/HCl, 2% PEG 40000, 2% Pluronic F68, pH 7.0 and 20 µl 1% streptavidin-latex as well as 50 µl in each case of an AFP standard (0, 50, 100, 1000 and 2000 ng/ml) were pipetted into cuvettes. The increase in the agglutination was measured at 405 nm in a Perkin-Elmer photometer between t=1 min and t=10 min.

The result of the immunoassay is shown in Table 4.

TABLE 4

| | Standard concentration (ng/ml) | | | | | |
| --- | --- | --- | --- | --- | --- | --- |
| | 0 | 50 | 100 | 500 | 1000 | 2000 |
| Absorbance (mean) | 44 | 51 | 60 | 151 | 299 | 547 |
| CV (%) | 17.6 | 12.8 | 12.2 | 8.4 | 4.5 | 1.9 |
| Standard 0 +3s range | 67 | — | — | — | — | — |

EXAMPLE 7

1. Antibodies

The monoclonal antibody directed against hepatitis B surface antigen (HBsAg), M-5A10 has been deposited under the deposit number ECACC 88072101 in compliance with the regulations of the Budapest Treaty. The characterization of precursors of the antibodies M-RF13 and M-RF18, which are also directed against HBsAg, is included in the publication "Analysis of the antigenic epitopes of hepatitis B surface antigen involved in the induction of a protective antibody response", Waters et al., Virus Research 22 (1991), 1–12 hereby incorporated by reference.

2. Production of conjugates 2.1 Ruthenylated F(ab')$_2$ conjugates

The production of F(ab')$_2$ fragments from the above-mentioned antibody M-5A10 was carried out in the same way as described in the first part of example 2, by means of pepsin digestion of the antibody and purification on DEAE-sepharose fast flow and sephacryl S 200.

The production of labelled antibody-fragments was brought about by reaction of the free amino groups of the F(ab')$_2$ fragment with the activated ruthenium present as N-hydroxy-succinimide ester ((bis-pyridyl)$_3^{2+}$-complex.

The ruthenium compound and the conditions of the coupling to antibody or rather antibody fragments are described in the patent application EP-A-0 199 804 abanboned the equivalent of U.S. application Ser. Nos. 666,987 abandoned and Ser. No. 789,113, U.S. Pat. No. 5,238,808 which are hereby incorporated by reference. For the rest the derivatization conditions correspond to the reaction with N-hydroxy-succinimide-X-biotin described in example 3 above.

The reaction of the antibody-fragment with the electrochemical luminescence marker was carried out in a molar ratio of 8:1 (marker compound to F(ab')$_2$ fragment).

2.2 Biotinylated conjugate

The production of antibody-biotin (DDS) derivatives was carried out under the same conditions as stated in example 3 for the conjugation with N-hydroxysuccinimide-X-biotin. Concerning the coupling method, the production and structure of the spacer molecule biotin-DADOO-DSS (=Bi (DDS)) has been described in PCT/EP94/00195, which described in Example 8 below as derived from example 1 of PCT/EP94/00195. The stoichiometries between marker and antibody are indicated in the tables 5–7.

The production of F(ab)'$_2$ fragments from the monoclonal antibodies was brought about by means of pepsin digestion in the same way as in example 2. The reduction of the F(ab')$_2$ to Fab' and the reaction with biotin-maleimidoethylamine (=Bi (MEA)) have also been carried out as shown in example 2. The molar ratio of the component amounted to 2 mole Bi (MEA) per mole Fab' fragment.

3. Conducting the measurements:

The performance if a biotinylated IgG-antibody was tested as compared with the performance of a biotinylated antibody Fab' fragment derivatized with maleimidoethylamine in an electrochemical luminescence HBsAg-assay. The ECL method of measurement employed has be en described in the publication "Electrogenerated chemiluminescence: An oxidative-reduction type ECL reaction sequence using tripropyl amine", Leland and Powell, J. Electrochem. Soc. 137, 10 (1990), 3127–3131 which is hereby incorporated by reference. The measurement was conducted on an origin 1.5 instrument with Orlo software.

TABLE 5

| biotinylated mab-derivative stoichiometry mab/biotin | 1.1. * 1:2 mol/mol | 1.2. 1:3.5 mol/mol | 1.2. 1:7.5 mol/mol | 1.2. 1:15 mol/mol |
|---|---|---|---|---|
| standards/samples | ECL-peak-intensity | ECL-peak-intensity | ECL-peak-intensity | ECL-peak-intensity |
| a) (0) | 8700 | 7271 | 5758 | 5659 |
| b) (0.6) | 20345 | 15960 | 11473 | 9857 |
| c) (2.6) | 69781 | 53368 | 29395 | 25623 |
| d) (18.4) | 487583 | 355338 | 233396 | 188941 |
| PS 1 | 300066 | 23326 | 13615 | 13992 |
| PS 2 | 57541 | 39397 | 28258 | 24016 |
| NS 1 | 7338 | 7311 | 6300 | 5947 |
| ratio b/a | 2.3 | 2.2 | 2.0 | 1.7 |
| ratio d/a | 56 | 49 | 41 | 33 |

* according to the present invention

TABLE 6

| biotinylated mab-derivative stoichiometry mab/biotin | 1.1. * 1:2 mol/mol | 2.2. 1:3.5 mol/mol | 3.2. 1:3.5 mol/mol |
|---|---|---|---|
| standards/samples | ECL-peak-intensity | ECL-peak-intensity | ECL-peak-intensity |
| a) (0) | 6183 | 4181 | 4344 |
| b) (0.5) | 43171 | 13852 | 13104 |
| c) (2.5) | 173700 | 52092 | 45444 |
| d) (16.5) | 2185630 | 288145 | 285171 |
| ratio b/a | 7.0 | 3.3 | 3.0 |
| ratio d/a | 354 | 69 | 66 |

* according to the present invention

The following components were employed:

|  | concentration | volume |  |  |
|---|---|---|---|---|
| Magnetic streptavidin-beads: | 500 µg/ml | 50 µl | 2.8 µm Dynal beads coated with streptavidin | |
| biotinylated antibodies or antibody fragments: | 200 ng/ml | 80 µl | <HBs>M-5A10-Fab'-Bi (MEA) | (1.1) |
|  |  |  | <HBs>M-5A10-IgG-Bi (DDS) | (1.2) |
|  |  |  | <HBs>RF13-Fab'-Bi (MEA) | (2.1) |
|  |  |  | <HBs>RF13-IgG-Bi (DDS) | (2.2) |
|  |  |  | <HBs>RF18-Fab'-Bi (MEA) | (3.1) |
|  |  |  | <HBs>RF18-IgG-Bi (DDS) | (3.2) |
| labelled antibody fragment: standards/sample: | 200 ng/ml | 80 µl 40 µl | <HBs>M-5A10-F(ab')$_2$-Ru(Bipy)$_2$ | |
| incubation-buffer: |  |  | 50 mM HEPES, 1% bovine serum albumin 0.15% Genapol X080, 10 µg/ml unspecific mouse-IgG | |
| incubation: |  |  | The mixture was incubated for 11 minutes at 37° C. and then transferred into a measuring cell which had been heated up to 28° C.. The detection was carried out at 28° C.. | |

The results of these tests are illustrated in the Tables 5–7. In table 5 four standards, a, b, c, d, were used with the HBsAg concentrations stated in parentheses, respectively (U/ml). Furthermore, two HBsAg-positive sera (PS1, PS2) and one HBsAg-negative serum (NS1) were tested.

The symbols in the tables 6 and 7 have a corresponding meaning.

TABLE 7

| biotinylated mab-derivative stoichiometry mab/biotin | Mab 1.1. * 1:2 mol/mol | Mab 2.1. * 1:2 mol/mol | Mab 3.1. * 1:2 mol/mol |
|---|---|---|---|
| standards/samples | ECL-peak-intensity | ECL-peak-intensity | ECL-peak-intensity |
| a) (0) | 13613 | 15759 | 15947 |
| b) (0.5) | 31628 | 46095 | 49401 |

TABLE 7-continued

| biotinylated mab-derivative stoichiometry mab/biotin | Mab 1.1. * 1:2 mol/mol | Mab 2.1. * 1:2 mol/mol | Mab 3.1. * 1:2 mol/mol |
|---|---|---|---|
| c) (16.5) | 701124 | 521073 | 667877 |
| PS 1 | 74049 | 63930 | 76044 |
| NS 1 | 13538 | 15362 | 15625 |
| ratio b/a | 2.3 | 2.9 | 3.1 |
| ratio c/a | 52 | 33 | 42 |

* according to the present invention

The results show that considerably improved dynamics are achieved when using the conjugates according to the invention as compared to the conjugates according to the prior art. This can be seen from the ECL-peak-intensity exhibiting a higher ratio of standards containing antigen (standards b), c), d) in tables 5–7) as compared to a standard not containing any antigen (standard a) in tables 5–7).

Furthermore, table 5 shows that the conjugate according to the invention exhibits a considerably more distinct signal for a positive serum than the comparative conjugates. It can be gathered therefrom that the conjugates according to the invention have a lower detection limit than the conjugates according to the prior art.

Moreover it was found that the conjugates according to the invention also exhibit a lower coefficient of variation than the prior art conjugates.

EXAMPLE 8

Synthesis of biotinoyl-amino-3,6-dioxaoctanvlamino-carbonyl-heptanoic acid-N-hydroxysuccinimide ester (biotin-DADOO-DSS or Biotin-DDS)

A solution of 561 mg (1.5 mmol) biotinoyl-1,8-diamino-3,6-dioxaoctane (biotin-DADOO, Boehringer Mannheim, Catalogue No. 1112074) in 25 ml freshly distilled dimethylformamide (DMF) is admixed with 0.21 ml (1.5 mmol) triethylamine and slowly added dropwise while stirring to a solution of 5.52 g (15 mmol) disuccinimidyl suberate (DSS, Boehringer Mannheim, Catalogue No. 1081730) in 50 ml freshly distilled DMF. IT is allowed to stir for 18 hours at room temperature. Afterwards the solution is evaporated on a rotary evaporator in an oil pump vacuum, the semi-solid residue is digested with ca. 70 ml water and the excess DSS is separated by filtration. The clear solution is lyophilized and the lyophilisate is subsequently digested with a small amount of THF. After suction filtering the solid product it is dried in a high vacuum.

Yield: 620 mg colourless powder.

TLC: Silica gel 60 (Merck); ethyl acetate/glacial acetic acid/water 6/3/1 (v/v/v); spraying with a mixture of 1/1 (v/v) of A) 2% $H_2SO_4$ in ethanol and B) 0.2% 4-dimethylaminocinnamaldehyde in ethanol and subsequently drying for 10 minutes at 100° C. yields a raspberry-red spot of the product at $R_f$=0.51.

$^1$H-NMR ($d_6$-DMSO): δ=1.10–1.80 (m, 14H), 2.05 (t, 4H), 2.65 (t, 2H), 2.80 (s, 4H), 2.60–3.60 (m, 11H), 3.50 (s, 4H), 4.05–4.40 (m, 2H), 6.36 (d, br, 2H), 7.80 (t, br, 2H).

What is claimed is:

1. A method for determining an analyte in a homogeneous immunoassay, consisting essentially of:
   (i) reacting a Fab' molecule with biotin, wherein said Fab' molecule is derived from an IgG molecule and has from 1–3 free SH groups in its hinge region and said biotin is either coupled to said free SH groups via a functional group attached to said biotin or via a spacer group coupled to biotin via a functional group, wherein the spacer group comprises an alkylene chain of from 4 to 16 carbon atoms to obtain an IgG derived Fab'-biotin conjugate or an IgG derived, Fab'-spacer biotin conjugate,
   (ii) adding said conjugate to a sample together with an agglutinatole particle coated with avidin or streptavidin, and
   (iii) determining agglutination as a determination of said analyte in said sample.

2. The method of claim 1, wherein said IgG is IgG1.

3. The method of claim 1, wherein said spacer is maleimidobutyryllysine.

4. The method of claim 1, wherein said IgG is IgGII.

5. The method of claim 4, wherein said spacer is maleimidoethylamine.

6. The method of claim 1, wherein said agglutinable particle is a latex particle.

7. Method for determining an analyte in a sample via a homogeneous immunoassay, comprising:
   (1) forming a composition of:
      (a) the sample,
      (b) a conjugate of an Fab' fragment and biotin, wherein said conjugate is produced by reducing an $F(ab')_2$ fragment having 1 to 3 free SH groups on its hinge region and reacting the Fab' fragment with biotin having a functional group suitable for the binding or wherein the Fab' is derivatized by a functional group wherein biotin is bound via the functional group and a spacer to at least one of said free SH groups of Fab' fragment to form a biotinylated Fab' fragment,
      (c) one substance selected from the group consisting of:
         (i) an analyte of interest or an analog of an analyte of interest, and,
         (ii) a binding partner or the analyte, wherein (i) and (ii) are linked to a label compound capable of being induced to electroluminescence, and
      (d) a plurality of particles having avidin or streptavidin on their surfaces,
   (2) inducing said label compound to electrochemiluminescence and measuring the luminescence emitted by the composition to determine the presence of said analyte of interest in the sample.

8. The method of claim 7 wherein the particles are magnetic particles.

9. The method of claim 7 wherein the label compound is a metal chelate.

10. The method of claim 9 wherein the metal chelate is selected from the group consisting of a ruthenium, osmium, rhenium, iridium, rhodium, platinum, indium, palladium, molybdenum, technetium, copper, chromium and tungsten metal chelate.

11. The method of claim 9, wherein the metal chelate is a ruthenium or osmium metal chelate.

12. The method of claim 9, wherein the label compound linked to the binding partner of the analyte, the analyte, or its analogue is a polydentate compound.

13. The method of claim 12 wherein the polydentate compound is bipyridyl, bipyrazyl, terpyridyl or phenantrolyl.

14. A method of determining an analyte in a homogeneous immunoassay consisting essentially of:

(i) reacting a Fab' molecule with biotin, wherein said Fab' molecule is derived from an IgG molecule and has from 1–3 free SH groups in its hinge region, and said biotin is either coupled to said free SH groups via a functional group attached to said biotin or via a spacer group coupled to biotin via a functional group, wherein the spacer group compresses an alkylene chain of from 4 to 16 carbon atoms to obtain an IgG derived Fab'-biotin conjugate or an IgG derived, Fab' spacer biotin conjugate, (ii) adding said conjugate to a sample together with an agglutinatable particle coated with avidin or streptavidin prepared by reacting avidin or streptavidin with a bifunctional compound having an N-hydroxysuccinimide group and an arylazide group under alkaline conditions of less than pH 9.5 in aqueous solution, to form a complex of said bifunctional compound and avidin or streptavidin, removing excess bifunctional compound, adding a latex particle to said aqueous solution, and irradiating said aqueous solution with a photon, to bind said complex to said latex particle, and (iii) determining agglutination as a determination of said analyte in said sample.

* * * * *